United States Patent
Cox et al.

(10) Patent No.: US 8,563,490 B2
(45) Date of Patent: Oct. 22, 2013

(54) MILD TO THE SKIN, FOAMING DETERGENT COMPOSITION

(75) Inventors: Trevor Frederick Cox, Wirral (GB); Robert John Crawford, Wirral (GB); Lee Garry Gregory, Huddersfield (GB); Sarah Louise Hosking, Wirral (GB); Panos Kotsakis, Manchester (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/636,711

(22) PCT Filed: Mar. 10, 2011

(86) PCT No.: PCT/EP2011/053648
§ 371 (c)(1),
(2), (4) Date: Sep. 24, 2012

(87) PCT Pub. No.: WO2011/120776
PCT Pub. Date: Oct. 6, 2011

(65) Prior Publication Data
US 2013/0040869 A1    Feb. 14, 2013

(30) Foreign Application Priority Data

Mar. 31, 2010  (EP) ..................... 10158795

(51) Int. Cl.
*A61K 8/00*    (2006.01)
(52) U.S. Cl.
USPC ........... 510/119; 510/123; 510/127; 424/70.1
(58) Field of Classification Search
None
See application file for complete search history.

(56) References Cited

U.S. PATENT DOCUMENTS

| | | | |
|---|---|---|---|
| 2,798,053 A | 7/1957 | Brown | |
| 4,741,855 A | 5/1988 | Grote et al. | |
| 5,417,879 A | 5/1995 | Hall et al. | |
| 5,520,839 A | 5/1996 | Hall et al. | |
| 5,654,192 A | 8/1997 | Ducreux et al. | |
| 5,756,471 A | 5/1998 | Hillion et al. | |
| 2011/0288000 A1 * | 11/2011 | Crawford et al. | 510/403 |

FOREIGN PATENT DOCUMENTS

| | | |
|---|---|---|
| DE | 19600743 A | 7/1997 |
| DE | 19648439 A | 5/1998 |
| EP | 0209783 A1 | 7/1986 |
| EP | 0499434 A1 | 8/1992 |
| EP | 550276 | 7/1993 |
| EP | 0965322 A1 | 12/1999 |
| EP | 1445302 A1 | 8/2004 |
| EP | 1953237 | 8/2008 |
| FR | 2792193 A1 | 10/2001 |
| FR | 2903005 | 1/2008 |
| FR | 2903005 A1 | 1/2008 |
| GB | 2445013 A | 6/2008 |
| JP | 2006070231 | 3/2006 |
| KR | 2004033376 | 4/2004 |
| WO | WO9534282 | 12/1995 |
| WO | WO9612469 | 5/1996 |
| WO | WO9816192 | 4/1998 |
| WO | WO0123517 A1 | 4/2001 |

OTHER PUBLICATIONS

PCT International Search Report International Application No. PCT/EP2011/053648 mailed May 11, 2011.
PCT Written Opinion of the International Searching Authority International Application No. PCT/EP2011/053648 mailed May 11, 2011.
International Preliminary Report on Patentability dated Jul. 3, 2012.

* cited by examiner

*Primary Examiner* — Necholus Ogden, Jr.
(74) *Attorney, Agent, or Firm* — Michael P. Aronson

(57) ABSTRACT

A mild to the skin, foaming detergent composition comprising: a) 1 to 20 wt % sophorolipid biosurfactant, b) 1 to 20 wt % of anionic surfactant selected from the group consisting of glycinate, sulphosuccinate, and mixtures thereof, c) 0 to 10 wt % foam boosting surfactant, d) 0 to 2 wt % additional electrolyte, e) 0 to 10 wt % additional additives, f) 40 to 98 wt % water. The anionic surfactant is preferably disodium laureth-3-sulphosuccinate. The electrolyte may be sodium chloride, the foam boosting surfactant may be olivamidopropyl betaine and the additional additives may be silicones, polymers, structurants, thickeners or pH adjusters. A preferred additive is a dispersed modified cellulose biopolymer as structurant. The composition is suitable for personal wash, shower gel and shampoo formulations.

8 Claims, No Drawings

MILD TO THE SKIN, FOAMING DETERGENT COMPOSITION

TECHNICAL FIELD

The present invention relates to mild to the skin, foaming aqueous detergent compositions comprising mixed surfactants and in particular to mixtures of anionic surfactant and biosurfactant. The compositions are suitable for use in personal wash, shower gel or shampoo formulations.

BACKGROUND

Sophorolipids are biosurfactants produced by several yeast species. In *Candida bombicola*, the hydrophilic moiety of the biosurfactant molecule is a disaccharide (i.e., sophorose), and the hydrophobic portion is an omega- or (omega-1)-hydroxy fatty acid attached to the sophorose via a glycosidic bond. The fatty acid chain, most commonly containing 16- and 18-carbon atoms, may be unsaturated and lactonized to the disaccharide. The disclosed potential applications of Sophorolipids include serving as environmentally friendly surfactants in oil recovery, and as active ingredient in detergent, cosmetic and lubricant formulations. Sophorolipids are also known to have antimicrobial activity. Sophorolipids produced by *Torulopsis* sp. consist of a dimeric sugar (sophorose) and a hydroxyl fatty acid linked by a B-glycosidic bond.

There are generally considered to be two types of sophorolipids, the acidic (non-lactonic) and the lactonic sophorolipids. The hydroxyl fatty acid moiety of the acidic Sophorolipids forms a macrocyclic lactone ring with the 4"-hydroxyl group of the sophorose by intramolecular esterification. Lactonic Sophorolipids have attracted more attention then their acidic counterparts. The acetylated lactonic Sophorolipids have been applied in cosmetics as antidandruff, bacteriostatic agents and deodorants.

Sophorolipids may be obtained from *Candida apicola*, *Candida bombicola* ATCC 22214, *Candida lipolytica* and *Candida bogoriensis* when grown on carbohydrates, hydrocarbons, vegetable oils or their mixtures. They are produced as a mixture of six to eight different hydrophobic sophorosides.

EP 499 434 (Unilever) discloses the improved oily soil detergency of mixtures of a sophorolipid (SOL-TUBS a sophoroselipid from technical University of Braunchweig, Germany); produced by torulosis bombicola. It comprised a mixture of four different sophorolipids, the main fatty acid chain length being $C_{18}$. Examples 5, 6 and 7 of this patent application use blends of sophorolipids with specified nonionic surfactants. The nonionic cosurfactants used were: Synperonic A3 (an alcohol ethoxylate containing a certain amount of branching in the hydrophobe and manufactured from petrochemical fatty alcohol by reaction with 3 moles of ethylene oxide), a $C_{12}$ 1,2-diol and a $C_{10}$ monoglycerolether. The application also suggests that the biosurfactants can be used with anionic surfactant: dialkyl sulphosuccinates are said to be of especial interest on page 7. There is no mention of mildness or foaming.

U.S. Pat. No. 5,417,879 (Unilever) also discloses combinations of glycolipid and non-glycolipid surfactants for oily/fatty soil detergency. Sophorolipids are mentioned among the glycolipids and dialkylsulphosuccinates are mentioned among the preferred non-glycolipid surfactants. However, all of the examples with sophorolipids use nonionic cosurfactants.

U.S. Pat. No. 5,520,839 (Unilever) makes a similar general disclosure and synergistic detergency claim, but also describes specific examples of dialkyl sulphosuccinates to include those in which both alkyl substituents contain at least 4 carbon atoms, and together contain 12 to 20 carbon atoms in total; such as di-$C_8$ alkyl sulphosuccinate. This surfactant was exemplified with rhamnolipid, but the sophorolipids were only exemplified in combination with nonionic surfactants.

DE 19600743 (Henkel) discloses combinations of sophorolipids and anionic surfactants. No disclosure of combinations with dialkoxy sulphosuccinates or alkyl glycinate is made.

EP 1 445 302 (Ecover) discloses a detergent composition comprising at least one glycolipid biosurfactant and at least one non-glycolipid surfactant. In several examples, a Sophorolipid (Sopholiance from methyl ester of rapeseed oil ex Soliance) was used. Foam quality when used in combination with various nonionic surfactants and also anionic surfactant (SLS) was investigated.

EP 1 953 237 (Ecover) discloses a method for producing short chain sophorolipids. It says that sophorolipids are one of the most promising biosurfactants, due to their high production yields and ease of recovery. It also says that they are mild to the skin.

WO 98/16192 (Alterna Inc) discloses a germicidal composition suitable for cleaning fruits, vegetables, skin and hair. The composition may comprise a mixture of anionic surfactant and sophorolipids biosurfactant. The anionic surfactants mentioned are those with biocidal activity: Sodium lauryl sulphate (SLS), Sodium lauryl ethoxy sulphate (SLES).

EP 550 276 (Unilever) describes a personal care composition comprising a mild and foaming glycolipid used with a co surfactant (e.g. SLS). The glycolipid is a uronic acid derivative. No synergy is observed for either mildness or foam between the biosurfactant and the SLS or SDS.

WO 96/12469 (Unilever) describes a personal care composition comprising a lipid, which may be a glycolipid such as a glycosyl glyceride of diacyl or dialkyl saccharides (eg a sugar ester), a surfactant and a deposition aid. Preferred mild surfactants include alkyl ether sulphate, alkyl glyceryl ether sulphate, sulphosuccinates, taurates, sarcosinates, sulphoacetates, alkyl phosphate, alkyl phosphate esters, acyl lactylate, and alkyl glutamates. Examples used SLES or APG with the sugar ester lipid.

DE 196 48 439 & DE 196 00 743 (Henkel) describe the use of a mixture of glycolipids, which specifically includes sophorolipids and a long list of possible anionic surfactants, including mono and dialkyl sulphosuccinates. In the only example for each document that uses sophorolipid, it is combined with SLS as anionic surfactant.

FR 2 792 193 (Lavipharm Lab) describes a cosmetic base comprising a composition rich in lipids of vegetable origin and at least one surfactant. A shampoo composition is disclosed with the lipids used in approx 1:1 ratio with a surfactant, which is itself a mixture of anionic and amphoteric surfactants. The anionic component is an alkyl sulphate.

U.S. Pat. No. 5,654,192 (Institut Francais du Petrole) discloses compositions containing an anionic and/or nonionic surfactant, and at least one glycolipid. The composition is used for decontaminating a polluted porous medium. Sulphosuccinates and sophorolipids are both mentioned. There are specific examples using combinations of sodium dioctyl sulphosuccinate and sophorolipids showing the synergistic effect on lowering of interfacial tension. Neither foaming, nor mildness to human skin is mentioned. No aqueous concentrated composition is disclosed. In use, the materials are mixed with water but there is then less than 1% of the sophorolipids.

JP 2006070231 A (Saraya), discloses a biodegradable liquid cleaning composition e.g. liquid body cleaning composition for jet washing. The composition contains sophorolipids comprising 90% or more acid-type sophorolipids. The compositions are used as a liquid body cleaning composition for jet washing. The biodegradable liquid cleaning composition has excellent cleaning power and low foaming property. The acid-type sophorolipid is chemically stable in the liquid cleaning composition.

KR 2004033376 A (LG Household & Healthcare Ltd) describes a cosmetics composition comprising sophorolipids. The cosmetics composition comprises, as an active ingredient, sophorolipids, which are produced from *Candida bombiocola* (ATCC 22214). The cosmetic composition has excellent sterilization effect as well as moisturising and softening effects on the skin. A cosmetics composition is characterized by comprising, as a biosurfactant, 0.01-10 weight % of sophorolipids. The composition is formulated into face lotion, nutritive emulsion, face cream and the like.

WO 9534282 (INST FRANCAIS DU PETROLE) discloses cosmetic and dermatological compositions containing sophorolipid (s) —as radical scavengers, elastase inhibitors and antiinflammatory agents.

There is an unmet need for a mild and high foaming surfactant system for use in personal care (cleaning) products that employs surfactant systems that can be considered relatively environmentally friendly.

SUMMARY OF THE INVENTION

According to the present invention there is provided a mild to the skin, foaming detergent composition comprising:
a) 1 to 20 wt % sophorolipid biosurfactant,
b) 1 to 20 wt % of anionic surfactant selected from the group consisting of glycinate, sulphosuccinate, and mixtures thereof,
c) 0 to 10 wt % foam boosting surfactant,
d) 0 to 2 wt % additional electrolyte,
e) 0 to 10 wt % additional detergent additives,
f) 40 to 98 wt % water.

The weight ratio a:b is preferably 3:1 to 1:3, most preferably 1.5:1 to 1:1.5.

It is preferred to select a) and b) to be both mild and foaming. However, if additional foaming is required than a foam boosting surfactant may be included as component c), the foam boosting surfactant is advantageously 2 to 8 wt % olivamidopropyl betaine, due to its mildness.

The anionic surfactant component b). advantageously comprises cocoyl glycinate (sodium salt) or dialkoxy sulphosuccinate (disodium salt).

The additional electrolyte component d) may comprise sodium chloride. The additional additives e) may comprise materials selected from the group: silicones, polymers, structurants thickeners, pH adjusters and mixtures thereof.

The invention also comprises use of a mixture of 1-20 wt % sophorolipids and 1-20 wt % anionic surfactant selected from the group consisting of glycinate, sulphosuccinate, and mixtures thereof in a detergent composition to increase the mildness to the skin of the composition. Especially it comprises use of the composition as a mild and foaming shampoo or body wash.

The invention results from the finding that a blend of a specific type of biosurfactant with a specific type of anionic surfactant shows increased mildness to skin with excellent foaming properties.

Mild to the skin means: that in the skin protein protection assay described as for example 1 below the absorbance measured is greater than 0.8%. The basis of the mildness assay is the enzymatic activity of Chymotrypsin on a chromogenic substrate. Surfactant mildness is assessed by the effect of a surfactant on the enzyme protein. A harsh surfactant will degrade Chymotrypsin, leading to a lower optical density reading in the reaction well. The enzyme used for this assay is a-Chymotrypsin from bovine pancreas. The enzyme used is the chromogenic substrate for Chymotrypsin, N-Succinyl-Ala-Ala-Pro-Phe-pNA. The 0.8 value is for the optical density at 450 nm of the system, and the units should be %, as in 0.8% of the incident light was transmitted. CHECK AGAINST EG1 etc.

Foaming means: that in the foaming assay described as Phase 2 below, the foam thickness doesn't decrease significantly within 10 minutes of agitation. The inclusion of the sulphosuccinates or the glycinate reduces the amount of relatively expensive sophorolipids biosurfactant as expected but surprisingly it confers further synergistic mildness and foaming benefits as described more fully below. Blends according to the invention give both mildness and foaming. Such a combination is desired for personal products applications such as shampoo, shower gel, skin cleansing compositions, foam bath or any other cleaning composition that comes into contact with skin during its use. Thus, hand dish washing compositions, hard surface cleaning applications and some laundry composition uses could also be made using the detergent compositions of the invention.

DETAILED DESCRIPTION OF THE INVENTION

The present invention relates to a personal wash shower gel or shampoo formulation containing a mixture of sophorolipid and glycinate surfactants, for improved skin protein protection. Specifically the present invention comprises the use of mixture of sophorolipids, with 1 to 20 wt % of selected anionic surfactant, preferably amilite, a cocoyl glycinate (sodium salt), for improved skin protein protection.

A preferred sophorolipid for such Personal Products applications, like hair shampoo, is Sopholiance S—ex Soliance. It is said to be a Candida Bombicola/Glucose/Methyl Rapeseedate Ferment (and) water (and) Potassium Sorbate. Some published analysis gives the raw material as 50% sophorolipid. It is believed that the material is mainly lactonic.

Short chain length sophorolipids (<015) are preferred.

The compositions may comprise 0-2 wt % other electrolyte, for example sodium chloride.

They may also comprise minor amounts (<5 wt %) of additives such as silicones, polymers, structurants, thickeners, pH adjusters etc.

Certain optional surfactants can be incorporated at low levels in the composition so long as they do not compromise the mildness of the composition. Examples of acceptable additional optional surfactants that can be used at low levels, typically under 3% and preferably under 2% are alcohol ethoxylates having greater that 7 ethylene oxide groups, alkyamphodiacetates, alkylamphodipropionates, alkyliminodipropionates, alkyl sacrosinate, alkyl ethoxy carboxylates, ethoxylated sorbitan monoesters of fatty acids, polyoxyethylene derivatives of polyol esters.

Apart from these optional surfactants and the claimed essential surfactants, other surfactants should be used at levels of less than 1 wt % of the total composition. Preferably alkyl sulfates and alkyl or alkyl aryl sulfonates, ethoxylated alkylphenols, ethanolamides of aliphatic acids are avoided altogether.

The compositions may further comprise a non-volatile, water-insoluble silicone at concentrations effective to provide hair or skin conditioning benefits. Such concentrations range from about 0.01% to about 5%, preferably from about 0.1% to about 5%, and most preferably from about 0.2% to about 3%, by weight of the composition. This silicone is insoluble in water and in the compositions, and is non-volatile. Typically, it will be intermixed in the composition to be in the form of a separate, discontinuous phase of dispersed, insoluble particles, also referred to as droplets. These droplets are typically suspended with an optional suspending agent described hereinafter. The silicone conditioning agent phase will comprise a silicone fluid conditioning agent and can also comprise other ingredients, such as a silicone resin to improve silicone fluid deposition efficiency or enhance appearance (especially when high refractive index (e.g. above about 1.46) silicone conditioning agents are used (e.g. highly phenylated silicones).

The silicone conditioning agents for use in the compositions preferably have a viscosity of from about 20 to about 2,000,000 centistokes, more preferably from about 1,000 to about 1,800,000 centistokes, even more preferably from about 50,000 to about 1,500,000 most preferably from about 100,000 to about 500,000 centistokes, as measured at 25° C.

Silicone fluids include silicone oils which are flowable silicone materials having a viscosity of less than 1,000,000 centistokes, preferably between about 5 and 1,000,000 centistokes, more preferably between about 10 and about 100,000 centistokes, at 25° C. Suitable silicone oils include polyalkyl siloxanes, polyaryl siloxanes, polyalkylaryl siloxanes, polyether siloxane copolymers, and combinations thereof. Silicone oils further include polyalkyl or polyaryl siloxanes containing substituent groups that include alkoxy, aryloxy, alkaryl, arylalkyl, arylalkenyl, alkamno, and ether-substituted, hydroxyl-substituted, and halogen-substituted aliphatic and aryl groups. The substituent groups can also include cationic amines and quaternary ammonium groups.

The aliphatic or aryl groups substituted on the siloxane chain may have any structure so long as the resulting silicones remain fluid at room temperature, are hydrophobic, are neither irritating, toxic nor otherwise harmful.

The average silicone particle size of the emulsified silicone in the composition is suitably less than 20 microns, preferably less than 10 microns. Ideally, it ranges from 0.15 to 2 microns, optimally from 0.2 to 1 micron.

Preferred non-volatile silicones are polyalkylsiloxane fluids, for example, polydimethylsiloxanes. These siloxanes are available, for example, from the General Electric Company in their Viscasil R and SF 96 series, and from Dow Corning in their Dow Corning 200 series.

Polyalkylaryl siloxane fluids may be used, for example, polymethylphenylsiloxanes. These siloxanes are available, for example, from the General Electric Company as SF 1075 methyl phenyl fluid or from Dow Corning as 556 Cosmetic Grade Fluid.

Polyether siloxane copolymers may be used, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide concentrations must be sufficiently low to prevent solubility in water and in the composition.

Suitable alkylamino substituted silicones include those known by the CTFA designation "amodimethicone". An especially preferred cationic polymer is known as "trimethylsilylamodimethicone".

Other silicone fluids are the insoluble silicone gums. These gums are polyorganosilxane materials having a viscosity at 25° C. of greater than or equal to 1,000,000 centistokes.

Another category of non-volatile, insoluble silicone fluid conditioning agents are the high refractive index silicones, having a refractive index of at least about 1.46, preferably at least about 1.48, more preferably at least about 1.52, most preferably at least about 1.55. The refractive index of the polysiloxane fluid will generally be less than about 1.70, typically less than about 1.60. In this context, polysiloxane "fluid" includes oils as well as gums. The high refractive index polysiloxane fluids contain a sufficient amount of aryl-containing substituents to increase the refractive index to the desired level. Aryl-containing substituents contain alicyclic and heterocyclic five and six membered aryl rings, and substituents containing fused five or six membered rings. The aryl rings themselves can be substituted or unsubstituted. Substituents include aliphatic substituents, and can include alkoxy substituents, acyl substituents, ketones, halogens (e.g., Cl and Br), amines, etc. Exemplary aryl-containing groups include substituted and unsubstituted arenes, such as phenyl, and phenyl derivatives such as phenyls with C1-C5 alkyl or alkenyl substituents, e.g., allylphenyl, methyl phenyl and ethyl phenyl, vinyl phenyls such as styrenyl, and phenyl alkynes (e.g. phenyl C2-C4 alkynes). Heterocyclic aryl groups include substituents derived from furan, imidazole, pyrrole, pyridine, etc. Fused aryl ring substituents include, for example, naphthalene, coumarin, and purine.

It is preferred to utilize high refractive index silicones in solution with a spreading agent, such as a silicone resin or a surfactant, to reduce the surface tension by a sufficient amount to enhance spreading.

Silicone resins can be included in the silicone conditioning agent. These resins are highly crosslinked polymeric siloxane systems.

Information about suitable silicones is available to the person skilled in the art, for example information on silicone fluids, gums, and resins, as well as manufacture of silicones, can be found in Encyclopedia of Polymer Science and Engineering, Volume 15, Second Edition, pp 204-308, John Wiley & Sons, Inc.

Cationic polymers may be employed to provide enhanced deposition of the non-volatile, water-insoluble silicone as well as conditioning benefits in their own right. The cationic conditioning polymer contains cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the shampoo composition. The average molecular weight of the cationic conditioning polymers is between about 10 million and about 5,000, preferably at least about 100,000, more preferably at least about 200,000, but preferably not more than about 2 million, preferably not more than about 1.5 million. The polymers also have a cationic charge density ranging from about 0.2 meq/gm to about 7 meq/gm, preferably at least about 0.4 meq/gm, more preferably at least about 0.6 meq/gm, but also preferably less than about 5 meq/gm, more preferably less than about 2 meq/gm, at the pH of intended use of the shampoo composition, which pH will generally range from about pH 3 to about pH 9, preferably between about pH 5 and about pH 8.

Any anionic counterions can be use in association with the cationic conditioning polymers so long as the polymers remain soluble.

Non-limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982).

Especially preferred cationic conditioning polymers are the cationic cellulose polymers especially like those polymers available from Amerchol Corp. (Edison, N.J.,) in their Polymer JR and LR series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CIFA) as Polyquaternium 24. These materials are available from Amerchol Corp. (Edison, N.J.,) under the trade name Polymer LM-200. The level of cationic cellulose in the composition can be in the range from about 0.01 to about 2%, preferably from about 0.1 to about 0.6%, and most preferably from about 0.15 to about 0.45%. Suitable optional modified natural polymers include cationic guar gum derivatives, such as guar hydroxypropyltrimonium chloride, specific examples of which include the Jaguar series commercially available from Celanese Corporation. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581.

Non limiting examples of suitable optional synthetic cationic polymers include copolymers of vinyl monomers having cationic protonated amine or quaternary ammonium functionality with water soluble spacer monomers such as acrylamide, methacrylamide, alkyl and dialkyl acrylamides, alkyl and dialkyl methacrylamides, alkyl acrylate, allyl methacrylate, vinyl caprolactone or vinyl pyrrolidone. The alkyl and dialkyl substituted monomers preferably have from C1 to C7 alkyl groups, more preferably from C1 to C3 alkyl groups. Other suitable spacer monomers include vinyl esters, vinyl alcohol (made by hydrolysis of polyvinyl acetate), maleic anhydride, propylene glycol, and ethylene glycol.

Other suitable optional synthetic polymers include protonated amino and quaternary ammonium monomers, for inclusion in the cationic polymers of the shampoo composition herein, include vinyl compounds substituted with dialkylaminoalkyl acrylate, dialkylaminoalkyl methacrylate, monoalaylaminoalkyl acrylate, monoalkylaminoalkyl methacrylate, trialkyl methacryloxyalkyl ammonium salt, trialkyl acryloyalyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the C1, C2 or C3 alkyls.

Other suitable optional synthetic polymers include amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably C1-C7 hydrocarbyls, more preferably C1-C3 alkyls.

Still other suitable optional synthetic polymers for use in the shampoo composition include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., U.S.A) under the LUVIQUAT tradename (e.g., LUVIQUAT FC 370); copolymers of 1-vinyl-2-pyrrolidone and dimethylaminoethyl methacrylate (refereed to in the industry by CTFA as Polyquaternium-11) such as those commercially available from ISP Corporation (Wayne, N.J., U.S.A.) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homopolymers and copolymers of unsaturated carboxylic acids having from 3 to 5 carbon atoms, as described in U.S. Pat. No. 4,009,256, which description is incorporated herein by reference.

The compositions of the present invention preferably further comprise thickening/suspending agents to ensure that any insoluble materials are stable. A variety of materials can be employed. These include swelling and associative polymers, finely divided crystalline or amorphous inorganic and organic materials that form networks, electrolytes and combinations thereof.

Organic polymers include carboxyvinyl polymers such as the copolymers of acrylic acid crosslinked with polyallylsucrose as described in U.S. Pat. No. 2,798,053, which description is incorporated herein by reference. Examples of these polymers include Carbopol 934, 940, 941, and 956, available from B. F. Goodrich Company and the alkali swellable acrylic latex polymers sold by Rohm and Haas under the ARYSOL or ACULYN trade names.

Other suitable suspending agents include xanthan gum at concentrations ranging from about 0.3% to about 3%, preferably from about 0.4% to about 1.2%, by weight of the shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent. Such combinations are described in U.S. Pat. No. 4,704,272.

Other suitable polymeric suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hydropylcellulose, hydroxypropyl methylcellulose, hydroxyethyl ethylcellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Optional crystalline organic suspending agents include acyl derivatives, long chain amine oxides, or combinations thereof, concentrations of which range from about 0.1% to about 5.0%, preferably from about 0.5% to about 3.0%, by weight of the shampoo compositions. When used in the shampoo compositions, these suspending agents are present in crystalline form. These suspending agents are described in U.S. Pat. No. 4,741,855, which description is incorporated herein by reference. These suspending agents include ethylene glycol esters of fatty acids preferably having from about 16 to about 22 carbon atoms. Examples include ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having C8-C22 chains may be used. Examples of suitable long chain amine oxides for use as suspending agents include alkyl (C16-C22) dimethyl amine oxides, e.g., stearyl dimethyl amine oxide. Another useful crystalline suspending agent is trihydroxystearin sold under the trade name THIXCIN R®.

Network forming inorganic materials include but are not limited to clays, and silicas. Examples of clays include smectite clay selected from the group consisting of bentonite and hectorite and mixtures thereof. Synthetic hectorite (laponite) clay is often used with an electrolyte salt capable of causing the clay to thicken (alkali and alkaline earth salts such as halides, ammonium salts and sulfates). Bentonite is a colloidal aluminium clay sulphate. Examples of silica include amorphous silica and include fumed silica and precipitated silica and mixtures thereof.

Associative polymers are those that incorporate hydrophobic groups that can form labile crosslinks alone or with the participation of surfactant micelles. An example of associative polymers the hydrophobically modified cross linked polyacrylates sold by Noveon under the PEMULEN trade name. Other example are the hydrophobically modified cellulose ethers and hydrophobically modified polyurethanes.

A particularly preferred class of thickening and suspending agent in the present invention are hydrophobically modified water-soluble nonionic polyols. Suitable hydrophobically modified water-soluble nonionic polyols for use herein are PEG 120 methyl glucoside dioleate (available from Amercol under the trade name GLUCAMATE DOE 120), PEG-150 pentaerythrityl tetrastearate (available from Croda under the trade name CROTHIX, PEG-75 dioleate (available from Kessco under the trade name PEG-4000 DIOLEATE and PEG-150 distearate (available from Witco under the trade name WITCONAL L32).

Long chain fatty esters of polyethylene glycol, e.g., PEG-150 distearate, are especially preferred thickening and suspending agents in the present invention. Although the PEG fatty esters can be used alone, it has been found that their effectiveness and efficiency can be greatly improved when they are combined with certain electrolytes. Especially preferred electrolytes for use in combination PEG-150 distearate, are sodium citrate and sodium chloride as they provide a synergistic thickening system that allows adequate thickening at low levels of inclusion in composition that have a low total concentration of surfactant, e.g., less than about 15 wt %. This is important in achieving mild tear-free formulations that provide excellent conditioning properties and are economical.

The above thickening and structuring agents can be used alone or in mixtures and may be present in an amount from about 0.1 wt % to about 10 wt % of the composition. When PEG-150 distearate/electrolyte mixtures are employed as the thickening system, the level of organic thickener can be substantially reduced to a level between about 0.1 to about 0.5 wt %, preferably between 0.2 wt % and 0.4 wt %.

A particularly preferred structuring agent is described in patent application PCT/EP2009/067916, the structuring system as described therein comprises 0.5 to 5 wt %, preferably 1 to 2 wt %, dispersed modified cellulose biopolymer, wherein the modification consists of the cellulose having its C6 primary alcohols oxidised to carboxyl moieties (acid/COOH—) on 10 to 70% of the glucose units and substantially all the remainder of the C6 positions occupied by unmodified primary alcohols, This type of structurant enables the formulator to replace surfactant required for structuring (but not for cleaning) with relatively low concentrations of low cost, partially oxidised, dispersed modified cellulose.

Such reduced surfactant compositions, which nonetheless maintain a thick gel-like consistency, allow suspension of sensory enhancers, such as capsules (including perfume containing encaps), beads, or glitter, which disperse rapidly in water upon dilution.

The modified cellulose biopolymer (i) is a water insoluble, water dispersible modified cellulose in which only a proportion of its C6 primary alcohol groups have been oxidised to acid groups. Cellulose where all such alcohols have been oxidised is called polyuronic acid or polyglucuronic acid. Such fully oxidised material is soluble in water. It is unsuitable for use in the present invention for two reasons. Firstly, the cost of the extra processing required to create more than 70% substitution of primary alcohols by carboxylic acid groups makes it not cost effective as a replacement for surfactant and second the highly oxidised material tends to include unwanted depolymerised cellulose, which leads to a reduction of yield of insoluble dispersible structurant.

In this specification, a modified cellulose biopolymer is said to be water soluble, if it leaves less than 10 wt % of its dry mass as undissolved residue when a 2 g dry sample is added to 1 litre of agitated demineralised water at 25° C.

Totally unoxidised (unmodified) cellulose is unable to function as a structurant. Oxidising the cellulose to have at least 10% of the primary alcohols converted to carboxylic acids makes the cellulose dispersible using high shear in water and when mixed within the surfactant system the resulting structured liquid or gel maintains the cellulose in a dispersed state so it does not settle over time.

The structurant may be derived from entirely renewable, non-petrochemical resources; this combines well with the biosurfactants used in the present invention. Several factors influence the choice of a suitable starting material. More porous unmodified cellulosic material will oxidise more rapidly. Characterisation of surface area or porosity is readily achieved by porosimetry or BET measurements. In general, those starting materials that oxidise more rapidly due to their low crystallinity and higher surface area and/or porosity, prove easier to disperse than those that oxidise less rapidly. The rate of oxidation is also affected by the dimensions of the particles of cellulose starting material; the reduction in rate for longer (>500 micron) fibres is significant. Fibres less than 500 microns long are therefore preferred for this reason and due to the added difficulty in agitation of the longer fibres. While oxidation results in significant gross particle size reduction, this does not compensate for decreased fibril surface accessibility in the long fibres. Celluloses that have not been previously subjected to acid hydrolysis are a preferred starting material, due to reactivity, cost and resultant product dispersibility. Relatively unrefined α-cellulose, for example filter aid fibres, provides one of the most readily oxidised and dispersed sources of cellulose. An unexpected advantage of the process of the invention is the ability to use unbleached starting materials that might be regarded as unsuitable for structuring a clear liquid detergent composition. This is because the oxidation process also serves to bleach coloured components, such as lignin, in such unbleached cellulose starting materials.

Because of its known specificity for primary alcohol oxidation TEMPO (and related nitroxy radical species) mediated oxidation of cellulose is preferred. The process proceeds well without cooling, at relatively high weight % cellulose in the initial suspension. Simple workup procedures afford clean material suitable for dispersion. Such TEMPO mediated oxidation of cellulose is described in the published literature and the skilled worker will be able as a matter of routine to adapt known methods to achieve the oxidation required by this invention.

While aqueous NaOCl/TEMPO/NaBr is a highly preferred oxidation system. There are a number of other systems available to the skilled worker, especially for large scale production. Among such systems, there may be mentioned use of peracetic acid or monoperoxysulfate salts (Oxone®) as the oxidant with 4-acetamido-2,2,6,6-tetramethylpiperidine-1-oxyl (4-acetamido-TEMPO) as the radical transfer catalyst or mediator and sodium bromide co-catalyst for the oxidation. Elimination of chlorine from the oxidation system is environmentally desirable.

The use of 4-acetamido-TEMPO as radical transfer catalyst is also advantageous as, although it has a higher molecular weight than TEMPO, it has significantly lower vapour pressure reducing potential exposure hazards. Many other 4-substituted TEMPO analogues exist, but many, such as 4-hydroxy-TEMPO exhibit poor stability. TEMPO on solid supports or on soluble polymers may be used.

Electrochemical oxidation is a potentially clean means of effecting oxidation of carbohydrate moieties, although mediation by a radical transfer catalyst (such as TEMPO) is still required.

Laccase mediated oxidation, which also requires a radical transfer catalyst (e.g. TEMPO) but replaces the oxidant with an enzyme, may advantageously be used.

Using the TEMPO system the degree of reproducibility of oxidation of cellulose from the same source is good.

By degree of oxidisation of the modified cellulose we refer to the percentage glucose units oxidised to carboxylic acid as measured by titration with sodium hydroxide. It is assumed that all oxidation takes place at the primary alcohol positions. A reasonable assumption, given that primary alcohol specific oxidation chemistry is employed. Furthermore it is assumed that all oxidation leads to carboxylic acid formation.

Degree of polymerisation (DP) does not seem greatly to influence the performance of the modified cellulose. The key thing is that the modified cellulose must remain insoluble.

During oxidation, there is some degradation of the cellulose allowing release of polymer chains. It is particularly advantageous to keep this to a minimum in order to increase the yield of the modified insoluble cellulose material suitable for structuring applications. We have determined that above 70% oxidisation, the yield is unacceptably low and the processing costs become unacceptably high.

The degree of oxidation of the modified cellulose should lie in the range 10 to 70%. As the degree of oxidation increases, the amount of soluble material produced will rise and this reduces the yield of insoluble structuring material, thus the higher degrees of oxidation confer no real structuring benefits. For this reason, it is preferred to restrict the degree of oxidation to 60%, or even 50% and the most preferred modified materials have degrees of oxidation even lower than 40 or sometimes even lower than 30%.

To achieve a high enough dispersibility/solubility for the modified cellulose to act as a structurant it must be oxidised to at least 10%. The exact amount of oxidation required for a minimum effect will vary according to the starting material used. Preferably, it is at least 15% oxidised and most preferably, at least 20% oxidised.

At small scale, high energy sonication is the preferred method to give the high shear necessary to achieve the aqueous dispersion of the modified cellulose. However, other techniques are more suitable for large scale applications. These include the use of a high speed and high shear stirrer, or a blender, or a homogeniser. Homogenisation may achieve higher levels of dispersed material than are attainable via sonication.

When degrees of oxidation of less than 10% are used, the partially oxidised cellulose proves too resistant to dispersion to produce a transparent or translucent mixture and higher energy input is required. Provided the lower limit of 10% is exceeded, those modified celluloses with a lesser degree of oxidation appear to provide greater structuring capacity once dispersed. This is attributed to less degradation of the material during oxidation and thus the existence of longer individual dispersed (not dissolved) fibrils. This may be because the structure of the cellulose starting material is partially retained, but the fibrils are rendered dispersible by the introduction of negatively charged functional groups on the surface during oxidation.

Oxidised, dispersed cellulose is a largely insoluble polymer that occurs in the form of well dispersed fibrils rather than isolated solvated polymer chains. The fibrils have a large aspect ratio and are thin enough to provide almost transparent dispersions. Carboxylate groups provide anionic surface charge, which results in a degree of repulsion between fibrils, militating against their reassociation into larger structures. Addition of acid to dispersions of oxidised cellulose results in separation of gelled material while at pH between ca 5-9 fibrils may be maintained in a dispersed form as the COO—salt of an appropriate counterion.

Aesthetic and Adjunct Ingredients: A wide variety of optional ingredients can be incorporated in the formulation provided they do not interfere with the mildness and foaming benefits provided by the composition. These include but are not limited to: perfumes, pearlizing and opacifying agents such as higher fatty alcohols, fatty acids, solid esters, nacreous "interference pigments" such as TiO2 coated micas, dyes and colorants, sensates such as menthol, preservatives including anti-oxidants and chelating agents, emulsion stabilizers, auxiliary thickeners, and mixtures thereof.

A variety of optional additional hair or skin benefit agents may be incorporated into the compositions. However, these agents should be selected consistent with the mildness of the composition. Such benefit agents include, but are not limited to: lipids such as cholesterol, ceramides, and pseudoceramides, additional non-silicone conditioning agents such as synthetic hydrocarbon esters, humectants such as glycerol, antimicrobial agents such as zinc pyridinethione, sunscreens, and mixtures thereof.

The compositions of the invention may take the form of shampoos. These may also include minor amounts of other ingredients such as antibacterial agents, foam boosters, pearlescers, perfumes, dyes, colouring agents, preservatives, thickeners, proteins, polymers such as silicone polymers, phosphate esters, sunscreens, antidandruff agents and buffering agents. Suitable thickeners include ANTIL 141 (Goldschmidt) which has the CTFA adopted name PEG 55 propylene glycol dioleate and comprises a polyoxyethylene-propylene glycol oleate, and REWOPOL PEG 6000 DS (ex Rewo) which is a polyethylene glycol distearate.

Formulation mildness to skin is a function of both lipid and protein integrity, that ensure limited trans-epidermal water loss. The stratum corneum chymotryptic enzyme (SCCE) and the stratum corneum tryptic enzyme (SCTE) are serine proteases of the kallikrein family, named KLK7/hK7 and KLK5/hK5, respectively. SCCE and SCTE are directly involved in desmosome degradation. A delicate balance between the proteolytic enzymes and their inhibitors is responsible for proper desquamation and good skin condition. We have found that blends, especially 1:1 mixtures, of sophorolipid and glycinate or sulphosuccinate offer better protein protection scores of the stratum corneum enzyme chymotrypsin than either of the single systems when added at equal concentrations. This synergy was not expected.

In addition to this mildness benefit, we have also found the surfactant combination to have extremely desirable foaming properties, as discussed further below.

Phase 1—Mildness Test (Chymotrypsin pNA Assay)

The basis of the surfactant protein mildness detecting assay used was the enzymatic activity of Chymotrypsin on a chromogenic substrate. A harsh surfactant degrades Chymotrypsin, leading to a lower absorbance reading. Any reading greater than 0.8% is taken to be a pass for mildness.

We tested non biosurfactants already described in the literature as mild together with some generally thought to be harsher, like SDS. We also tested a number of biosurfactant and other non-petrochemical surfactants. These surfactants were tested alone and in pairs. Tests were repeated with the further addition of a known naturally derived foam booster.

The data includes the double system combinations in order of ranking when compared to the single system controls. Only the milder systems were explored further to determine their foaming properties. Hence, SLES/Sophorolipid (is), which was not sufficiently mild, was not explored further in terms of foaming. All the double surfactant systems performing well in mildness/cmc/compatibility/green credentials were taken through to Phase 2, where they were tested for foaming.

Phase 2—Foaming Test

We tested all the milder surfactant combinations for foaming. The aim of the foam test was to differentiate between the foaming properties of the chosen systems on the basis of foam thickness and foam stability. Aqueous solutions of the surfactant mixtures were treated with a homogenizer, under a standard set of conditions, to create foam and then the extent and stability of the foam were assessed by turbidity measurements.

The main differentiating feature was the thickness of the foam after 10 minutes compared with its initial thickness. The systems exhibiting a thicker foam that was stable over the 10 minutes, i.e. showed little sign of collapse, were ranked higher than those with a thick foam that collapsed quickly or those with only a small amount of foam. Any system that did not pass the 10 minute test was discarded as insufficiently foaming.

Some, but not all, blends of the sophorolipid with other mild surfactants were found to exhibit increased mildness and foaming compared to the prior art systems using SLES/SLS surfactants as the non biosurfactant components.

EXAMPLE 1

For the skin protein protection assay, 70 µl stock buffer solution (33 mM of Tris pH8.0, 180 mM of NaCl, 1 mM of $CaCl_2$), 10 µl substrate stock solution (Ala-Ala-Pro-Phe-pNA; 4 mg/ml) and 20 µl enzyme (α-Chyotrypsin; 10 ng per well) were added to the wells of a 96-well plate together with 100 ul of the formulations pre-diluted 1:10 in water. Reaction mixes were incubated for 45 minutes before colorimetric measurements were taken at 405 nm by a SpectraMax plate reader.

Natural formulations were prepared as described in Table 1. The key to the surfactant systems is given in Table 2.

TABLE 1

| INGREDIENT | % FORMULATION (w/w) |
|---|---|
| Surfactant (single) | 15 |
| Surfactant (double) | 15 |
| NaCl | 0.5 |

TABLE 2

| Surfactant code | Surfactant type | Trade name | Chemical name (class) |
|---|---|---|---|
| a | Amphoteric | Miranol Ultra C-32 (Rhodia) | Sodium Lauroamphoacetate (Betaine derivative) |
| b | Nonionic | Plantacare 2000 UP (Cognis) | $C_{8-16}$ Fatty Alcohol Polyglycoside (APG) |
| c | Anionic | Medialan ® LD (Clariant) | Sodium Lauroyl Sarcosinate (Sarcosinate) |
| d | Anionic | Crodasinic CS30 Croda) | Sodium Cocoyl Sarcosinate (Sarcosinate) |
| e | Anionic | Makanate EL (McIntyre) | Disodium Laureth Sulphosuccinate (Sulphosuccinate) |
| f | Anionic | Amilite GCS-11 (Ajinomoto USA) | Sodium Cocoyl Glycinate (Glycinate) |
| g | Nonionic | Eucarol AGE ET (Lamberti) | Sodium Coco Glucoside Tartarate (APG ester) |
| h | Nonionic | Juazirine (Naturactiva) | Saponin extract from *Zizyphus joazero* |
| i | Biosurfactant | Sopholiance S (Soliance) | Sophorolipid (Biosurfactant) |
| j | Anionic | Pationic 138C (Rita) | Sodium Lauroyl Lactylate (Acyl Lactylate) |
| k | Biosurfactant | JBR425 (Jeneil) | Ramnolipid (Biosurfacant) |
| l | Amphoteric | Hostapon CGN (Clariant) | Sodium Cocoyl Glutamate (Acyl Glutamate) |
| s | Anionic | SLES-1EO | Sodium Lauryl Ether Sulphate (1EO) |

Table 3 shows Single system protein protection scores for single surfactant systems.

TABLE 3

| | Mildness | |
|---|---|---|
| single | Lsmean | StdErr |
| aa | 1.08 | 0.06 |
| bb | 1.23 | 0.06 |

TABLE 3-continued

| | Mildness | |
|---|---|---|
| single | Lsmean | StdErr |
| cc | 0.64 | 0.06 |
| dd | 0.80 | 0.06 |
| ee | 0.93 | 0.06 |
| ff | 0.89 | 0.06 |
| gg | 0.92 | 0.06 |
| hh | 0.36 | 0.06 |
| ii | 0.93 | 0.06 |
| jj | 0.15 | 0.06 |
| kk | 0.39 | 0.06 |
| ll | 0.48 | 0.06 |
| ss | 0.53 | 0.04 |

The terms used in the tables have the following meanings:
Lsmean—the least squares mean of Absorbance values for the treatment—adjusted for number of replicates or "run number" in the experiment (n=4).
StdErr—the standard error for the treatment
double—1 the "extra" mildness of the treatment over the first single surfactant (e.g. ac-aa);
double—2 the "extra" mildness of the treatment over the second single surfactant (e.g. ac-cc);
StdErr—the standard error of double—1;
tValue—the t-value to see if double—1 is significantly different from zero;
Prob—the p-value for the tValue;
tValue—the t-value to see if double—2 is significantly different from zero;
Prob—the p-value for the tValue.
IND=1 if the combination is better than ALL other singles.

Table 4 shows the double systems protein protection scores. In Table 4 bf (1.34) is better than aa (1.08), bb (1.23), . . . ss (0.53). IND=0 if the combination is not better than all other singles (e.g. of (1.13) is not better than bb (1.23) and so this double cannot beat all singles).

If Prob <0.05 and IND=1, then there is clear significance and synergistic mildness for the particular surfactant system. Thus in Table 4 the only doubles to:
a) outperform all singles; and
b) be significantly different from their corresponding singles are ei (Disodium Laureth Sulphosuccinate with Sophorolipid) and fi (Sodium Cocoyl Glycinate with Sophorolipid). bf=APG/glycinate. Prob. is too high for that combination.

TABLE 4

| surf | Ls mean | Std Err | Double-1 | Std Err | t Value | Prob | Double-2 | Std Err | t Value | Prob | IND |
|---|---|---|---|---|---|---|---|---|---|---|---|
| af | 1.13 | 0.08 | 0.06 | 0.10 | 0.56 | 0.57 | 0.25 | 0.10 | 2.50 | 0.01 | 0 |
| ai | 1.21 | 0.08 | 0.14 | 0.10 | 1.40 | 0.16 | 0.28 | 0.10 | 2.89 | 0.00 | 0 |
| bf | 1.34 | 0.08 | 0.11 | 0.10 | 1.15 | 0.25 | 0.45 | 0.10 | 4.61 | 0.00 | 1 |
| cg | 0.95 | 0.08 | 0.31 | 0.10 | 3.15 | 0.00 | 0.03 | 0.10 | 0.29 | 0.77 | 0 |
| ck | 0.73 | 0.08 | 0.09 | 0.10 | 0.95 | 0.34 | 0.34 | 0.10 | 3.46 | 0.00 | 0 |
| dg | 1.15 | 0.08 | 0.35 | 0.10 | 3.59 | 0.00 | 0.23 | 0.10 | 2.36 | 0.02 | 0 |
| di | 1.02 | 0.08 | 0.22 | 0.10 | 2.25 | 0.03 | 0.09 | 0.10 | 0.93 | 0.35 | 0 |
| dk | 0.85 | 0.08 | 0.04 | 0.10 | 0.43 | 0.66 | 0.45 | 0.10 | 4.62 | 0.00 | 0 |
| ef | 1.10 | 0.06 | 0.18 | 0.09 | 2.05 | 0.04 | 0.21 | 0.09 | 2.48 | 0.01 | 0 |
| eg | 1.11 | 0.08 | 0.19 | 0.10 | 1.91 | 0.06 | 0.19 | 0.10 | 1.97 | 0.05 | 0 |
| ei | 1.23 | 0.08 | 0.31 | 0.10 | 3.14 | 0.00 | 0.30 | 0.10 | 3.06 | 0.00 | 1 |
| fg | 1.11 | 0.08 | 0.22 | 0.10 | 2.21 | 0.03 | 0.74 | 0.10 | 7.48 | 0.00 | 0 |
| fi | 1.25 | 0.08 | 0.36 | 0.10 | 3.69 | 0.00 | 0.32 | 0.10 | 3.25 | 0.00 | 1 |
| gi | 1.09 | 0.06 | 0.17 | 0.09 | 2.02 | 0.04 | 0.16 | 0.09 | 1.89 | 0.06 | 0 |
| gl | 0.96 | 0.08 | 0.04 | 0.10 | 0.37 | 0.72 | 0.48 | 0.10 | 4.93 | 0.00 | 0 |
| kl | 0.58 | 0.06 | 0.19 | 0.09 | 2.18 | 0.03 | 0.10 | 0.09 | 1.19 | 0.23 | 0 |
| ks | 0.62 | 0.06 | 0.23 | 0.09 | 2.64 | 0.01 | 0.09 | 0.08 | 1.18 | 0.24 | 0 |
| is | 0.67 | 0.06 | −0.26 | 0.09 | −3.04 | 0.00 | 0.14 | 0.08 | 1.89 | 0.06 | 0 |

The invention claimed is:

1. A mild to the skin, foaming personal wash, shower gel or shampoo composition comprising:
   a) 1 to 20 wt % sophorolipid biosurfactant,
   b) 1 to 20 wt % of anionic surfactant selected from the group consisting of cocoyl glycinate, disodium laureth sulphosuccinate, and mixtures thereof,
   c) 0 to 10 wt % foam boosting surfactant,
   d) 0 to 2 wt % additional electrolyte,
   e) 0 to 10 wt % additional detergent additives,
   f) 40 to 98 wt % water.

2. A composition according to claim 1, wherein component b) is cocoyl glycinate (sodium salt).

3. A composition according to claim 1, wherein component b) is disodium laureth sulfosuccinate.

4. A composition according to claim 1, wherein the additional electrolyte component d) comprises sodium chloride.

5. A composition according to claim 1, comprising 2 to 8 wt % olivamidopropyl betaine, as foam boosting surfactant component c).

6. A composition according to claim 1, wherein the additional additives e) comprise materials selected from the group: silicones, polymers, structurants thickeners, pH adjusters and mixtures thereof.

7. A composition according to claim 1 wherein component e) comprises 0.5 to 5 wt %, dispersed modified cellulose biopolymer as a structurant, wherein the modification consists of the cellulose having its C6 primary alcohols oxidised to carboxyl moieties (acid/COOH—) on 10 to 70% of the glucose units and substantially all the remainder of the C6 positions occupied by unmodified primary alcohols.

8. The composition according to claim 1 wherein the weight ratio of component a) to component b), a:b, is 1.5:1 to 1:1.5.

* * * * *